United States Patent
Burgess

(10) Patent No.: US 10,577,357 B2
(45) Date of Patent: Mar. 3, 2020

(54) INHIBITORS OF LDLR-PCSK9 PROTEIN-PROTEIN INTERACTION AND METHODS OF THEIR USE

(71) Applicant: The Texas A&M University System, College Station, TX (US)

(72) Inventor: Kevin Burgess, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/334,285

(22) PCT Filed: Sep. 19, 2017

(86) PCT No.: PCT/US2017/052292
§ 371 (c)(1),
(2) Date: Mar. 18, 2019

(87) PCT Pub. No.: WO2018/053517
PCT Pub. Date: Mar. 22, 2018

(65) Prior Publication Data
US 2019/0211001 A1    Jul. 11, 2019

Related U.S. Application Data

(60) Provisional application No. 62/396,658, filed on Sep. 19, 2016.

(51) Int. Cl.
| | | |
|---|---|---|
| C07D 241/04 | (2006.01) |
| C07D 241/12 | (2006.01) |
| C07D 403/06 | (2006.01) |
| C07D 405/14 | (2006.01) |
| A61P 3/06 | (2006.01) |
| C07D 233/02 | (2006.01) |
| C07D 403/14 | (2006.01) |

(52) U.S. Cl.
CPC ............. *C07D 405/14* (2013.01); *A61P 3/06* (2018.01); *C07D 233/02* (2013.01); *C07D 403/14* (2013.01)

(58) Field of Classification Search
CPC ... C07D 241/04; C07D 241/12; C07D 403/06
See application file for complete search history.

(56) References Cited

U.S. PATENT DOCUMENTS

| 2004/0157264 A1 | 8/2004 | Sharma et al. |
| 2008/0058397 A1 | 3/2008 | Old |
| 2009/0170920 A1 | 7/2009 | Chen et al. |

FOREIGN PATENT DOCUMENTS

WO    2011/000945 A2    1/2011

OTHER PUBLICATIONS

International Search Report and Written Opinion dated Nov. 7, 2017, issued in International Application No. PCT/US2017/052292, filed Sep. 19, 2017, 9 pages.

*Primary Examiner* — Bruck Kifle
(74) *Attorney, Agent, or Firm* — Wolf, Greenfield & Sacks, P.C.

(57) ABSTRACT

Compounds that disrupt the interaction between PCSK9 and LDLR, compositions that include the compounds, and methods for making and using the compounds and compositions.

15 Claims, 7 Drawing Sheets

| KB22 | MW | SPR | | LDL-uptake assay | | Qikprop | | |
|---|---|---|---|---|---|---|---|---|
| | | $K_d$ (µM) | # | %LDL uptake at 5 µM | # | $logP_{o/w}$ | PSA | docking score |
| 34 | 695 | 23.6 ± 5.3 | 1 | 45.8 ± 4.7 | 1 | -5.7 | 366 | -2.84 |
| 31 | 683 | 97 | 3 | 35.9 ± 2.8 | 2 | -2.6 | 319 | -3.41 |
| 30 | 655 | N/A | | 34.7 ± 4.2 | 3 | -2.0 | 278 | -2.31 |
| 35 | 677 | 38.4 ± 9.6 | 2 | 23.6 ± 4.7 | 4 | -4.4 | 338 | -1.07 |
| 37 | 710 | N/A | | 17.6 ± 8.8 | 5 | -8.6 | 419 | -6.15 |
| 38 | 710 | N/A | | 13.3 ± 3.8 | 6 | -8.6 | 419 | -4.77 |
| 41 | 711 | N/A | | 11.3 ± 2.6 | 7 | -7.1 | 416 | -6.29 |

*Fig. 3*

INHIBITORS OF LDLR-PCSK9 PROTEIN-PROTEIN INTERACTION AND METHODS OF THEIR USE

CROSS-REFERENCE TO RELATED APPLICATION

This application claims the benefit of U.S. Application No. 62/396,658, filed Sep. 19, 2016, expressly incorporated herein by reference in its entirety.

STATEMENT OF GOVERNMENT LICENSE RIGHTS

This invention was made with Government support under R41HL126346 and R41 GM108153-01A1 awarded by the National Institutes of Health. The Government has certain rights in the invention.

FIELD OF THE INVENTION

The present invention is directed to compounds that are inhibitors of LDLR-PCSK9 protein-protein interaction and methods for using the compounds for lowering cholesterol.

BACKGROUND OF THE INVENTION

Proprotein convertase subtilisin kexin type 9 (PCSK9) is a serine protease involved in regulating the levels of the low density lipoprotein receptor (LDLR) protein. Experiments have shown that adding PCSK9 to HepG2 cells lowers the levels of cell surface LDLR that increasing PCSK9 protein levels decreases levels of LDLR protein in the liver, and that PCSK9 knockout mice have increased levels of LDLR in the liver. PCSK9 has been shown to directly interact with the LDLR protein.

Various human PCSK9 mutations that result in either increased or decreased levels of plasma LDL-C have been identified. Several mutations in human PCSK9 cause gain-of-function effects in humans, including hypercholesterolemia, increased LDL-C cholesterol levels, and increased risk of coronary heart disease. Even rarer human PCSK9 mutations induce loss-of-function, resulting in lowered LDL-C levels and an 88% reduction in coronary heart disease risk.

Evidence demonstrates that PCSK9, in particular, lowers the amount of hepatic LDLR protein and thus compromises the liver's ability to remove LDL cholesterol from the circulation. The data indicates that PCSK9 action leads to increased LDL-C by lowering LDLR protein levels.

Accordingly, there is substantial evidence indicating that PCSK9 plays a role in the regulation of LDL; that the expression or upregulation of PCSK9 is associated with increased plasma levels of LDL cholesterol, that the corresponding inhibition or lack of expression of PCSK9 is associated with reduced LDL cholesterol plasma levels; and that decreased levels of LDL cholesterol have been found to confer protection against coronary heart disease.

Reductions in LDL cholesterol levels have been directly related to the rate of coronary events and moderate lifelong reduction in plasma LDL cholesterol levels has been found to correlate with a substantial reduction in the incidence of coronary events. Accordingly, there is great benefit to be reaped from the managed control of LDL cholesterol levels.

A need exists for the identification of agents that may be used to modulate cholesterol levels and block or inhibit or neutralize the activity of PCSK9. The present invention advances these interests by providing novel antagonists of PCSK9 for use for in blocking, inhibiting or neutralizing one or more of the activities of PCSK9 and/or in blocking the interaction of PCSK9 with LDLR and/or for the treatment of therapeutic conditions identified herein especially those involving or associated with high or aberrant lipid or cholesterol levels.

SUMMARY OF THE INVENTION

The present invention provides compounds that disrupt the interaction between PCSK9 and LDLR, compositions that include the compounds, and methods for making and using the compounds and compositions.

In one aspect, the invention provides a compound having formula (I)

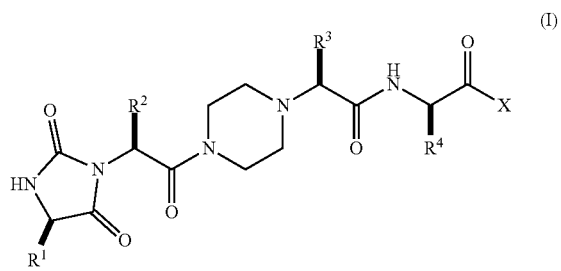

or a stereoisomer, or a pharmaceutically acceptable salt or ester thereof, wherein X is selected from $NH_2$, OH, $NH(CH_2)_nCO_2H$, where n is an integer from 1 to 8, and

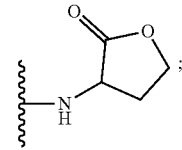 [SMILES: *NC1CCOC1=O]

$R^1$, $R^2$, and $R^4$ are independently selected from the group consisting of side chains for genetically encoded amino acids, their enantiomers (e.g., non-natural amino acids), and —$CH_2CN$; and $R^3$ is selected from the group consisting of side chains for genetically encoded amino acids, their enantiomers (e.g., non-natural amino acids), —$CH_2CN$, and a substituent having formula (II):

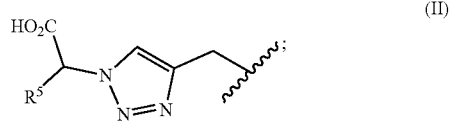

and $R^5$ is selected from the group consisting of side chains for genetically encoded amino acids and their enantiomers (e.g., non-natural amino acids).

In another aspect, the invention provides a compound having formula (IA)

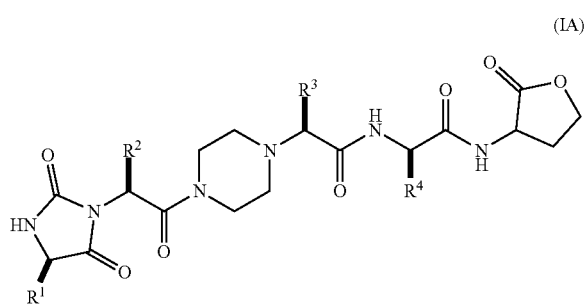

(IA)

or a stereoisomer or a pharmaceutically acceptable salt thereof,
wherein
$R^1$, $R^2$, $R^3$, and $R^4$ are independently selected from the group consisting of side chains for genetically encoded amino acids, their enantiomers (e.g., non-natural amino acids) and —$CH_2CN$ (as an analog of asparagine).

In yet another aspect, the invention provides a compound having formula (IB)

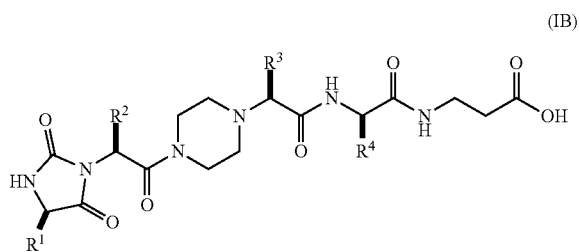

(IB)

or a stereoisomer or a pharmaceutically acceptable salt or ester thereof,
wherein
$R^1$, $R^2$, $R^3$, and $R^4$ are independently selected from the group consisting of side chains for genetically encoded amino acids, their enantiomers (e.g., non-natural amino acids), and —$CH_2CN$.

In certain embodiments, $R^1$ is an amino acid side chain selected from the group consisting of side chains of asparagine (—$CH_2CONH_2$), aspartic acid (—$CH_2CO_2H$), glutamine (—$CH_2CH_2CONH_2$), glutamic acid (—$CH_2CH_2CO_2H$), and valine (—$CH(CH_3)_2$). In certain of these embodiments, $R^1$ is the amino acid side chain of asparagine or aspartic acid.

In certain embodiments, $R^2$ is an amino acid side chain selected from the group consisting of side chains of cysteine (—$CH_2SH$), asparagine (—$CH_2CONH_2$), and leucine (—$CH_2CH(CH_3)_2$). In certain of these embodiments, $R^2$ is the amino acid side chain of leucine or cysteine.

In certain embodiments, $R^3$ is an amino acid side chain selected from the group consisting of side chains of asparagine (—$CH_2CONH_2$), aspartic acid (—$CH_2CO_2H$), and valine (—$CH(CH_3)_2$). In certain embodiments, $R^3$ is —$CH_2CN$. In certain of these embodiments, $R^3$ is the amino acid side chain of asparagine, leucine, or —$CH_2CN$.

In certain embodiments, $R^4$ is an amino acid side chain selected from the group consisting of side chains of lysine (—$CH_2CH_2CH_2CH_2NH_2$), arginine (—$CH_2CH_2CH_2NHC$ (=$NH)NH_2$), histidine (—$CH_2$—$C_3H_3N_2$), and tryptophan (—$CH_2$—$C_8H_6N$). In certain of these embodiments, $R^4$ is the amino acid side chain of arginine.

In another aspect, the invention provides a pharmaceutical composition, comprising a compound of the invention, or stereoisomer or pharmaceutically acceptable salt or ester thereof, and a pharmaceutically acceptable carrier.

In a further aspect, the invention provides methods for using the compounds and compositions of the invention.

In one embodiment, the invention provides a method for treating or preventing a condition associated with elevated serum cholesterol levels in a subject, comprising administering to a subject in need thereof an effective amount of a compound of the invention, or stereoisomer or pharmaceutically acceptable salt or ester thereof.

In another embodiment, the invention provides a method for lowering serum cholesterol levels in a subject, comprising administering to a subject in need thereof an effective amount of a compound of the invention, or stereoisomer or pharmaceutically acceptable salt or ester thereof.

In a further embodiment, the invention provides a method for increasing LDLR protein level in a subject, comprising administering to a subject in need thereof an effective amount of a compound of the invention, or stereoisomer or pharmaceutically acceptable salt or ester thereof.

In another embodiment, the invention provides a method for treating or preventing disorders of cholesterol or lipid homeostasis and disorders and complications associated therewith (e.g., hypercholesterolemia, hyperlipidemia, hypertriglyceridaemia, sitosterolemia, atherosclerosis, arteriosclerosis, coronary heart disease, metabolic syndrome, acute coronary syndrome, vascular inflammation, xanthoma and related conditions) in a subject, comprising administering to a subject in need thereof an effective amount of a compound of the invention, or stereoisomer or pharmaceutically acceptable salt or ester thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 3 summarizes select properties ($K_d$ (μm), LDL uptake) of representative compounds of the invention.

DETAILED DESCRIPTION OF THE INVENTION

Figure 1:
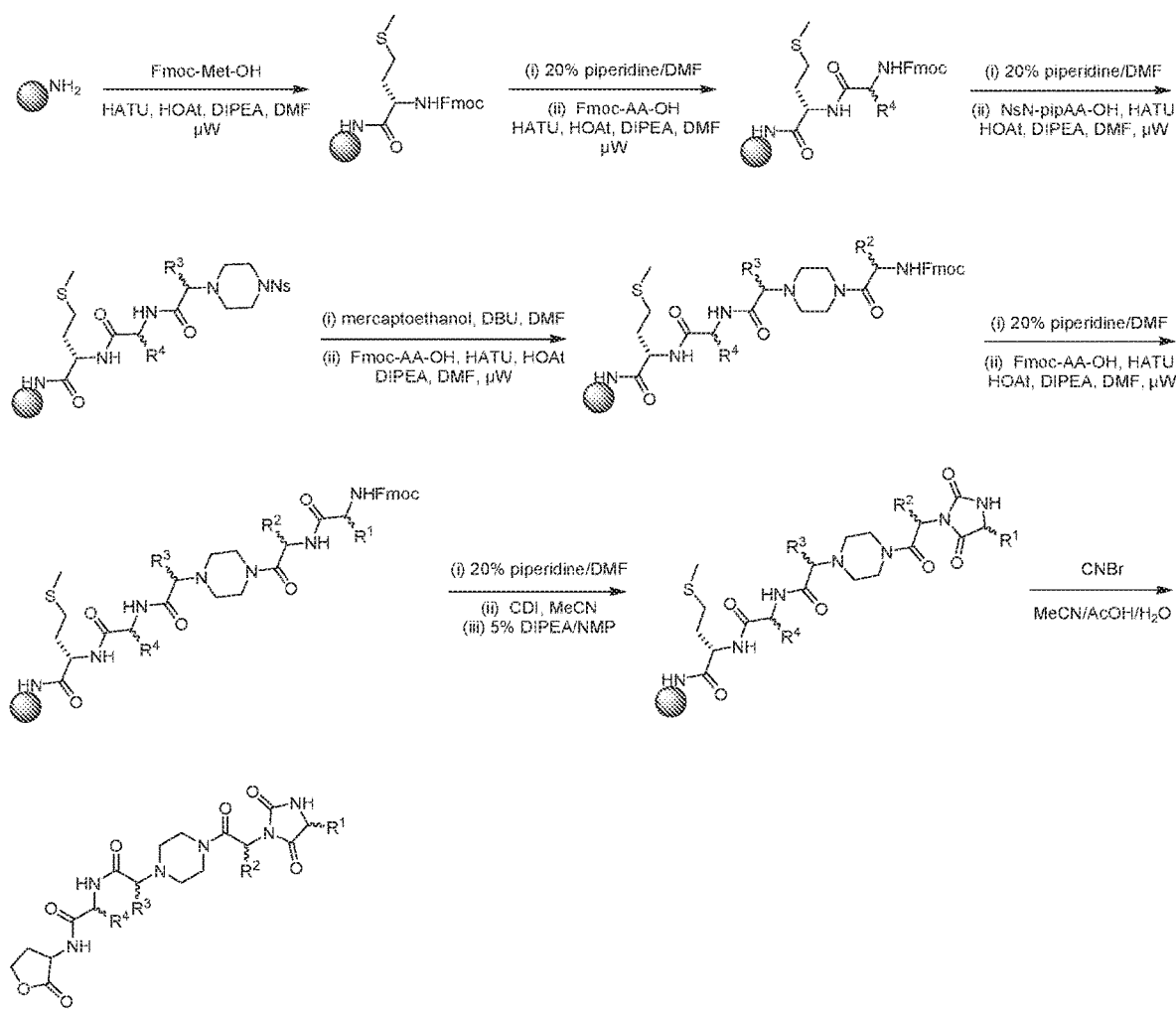
FIG. 1 is a schematic illustration of the preparation of representative compounds of the invention.

The present invention provides novel compounds that disrupt the interaction between PCSK9 and LDLR, compositions that include the compounds, and methods for making and using the compounds and compositions.

Proprotein convertase subtilisin kexin type 9 (PCSK9) is a serine protease involved in regulating the levels of the low density lipoprotein receptor (LDLR) protein. PCSK9 is a prohormone-proprotein convertase in the subtilisin (S8) family of serine proteases.

In certain embodiments, the compounds of the invention interfere with, block, reduce or modulate the interaction between PCSK9 and LDLR. In some embodiments, the compounds of the invention modulate or alter LDLR's ability to bind PCSK9. In some embodiments, the compounds of the invention bind to LDLR in a location and/or manner that prevents PCSK9 binding.

In one aspect, the invention provides compounds having formula (I)

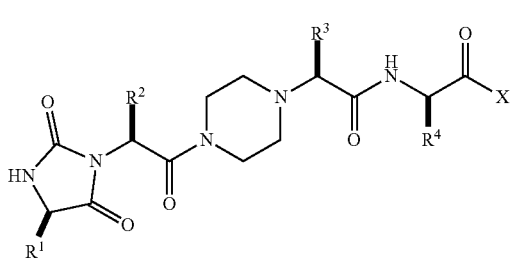

(I)

or a stereoisomer or a pharmaceutically acceptable salt or ester thereof, wherein X is selected from $NH_2$, OH, $NH(CH_2)_nCO_2H$, where n is an integer from 1 to 8, and

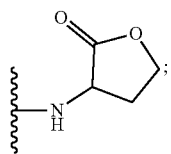 [SMILES: *NC1CCOC1=O]

$R^1$, $R^2$, and $R^4$ are independently selected from the group consisting of side chains for genetically encoded amino acids, their enantiomers (e.g., non-natural amino acids), and —$CH_2CN$; and $R^3$ is selected from the group consisting of side chains for genetically encoded amino acids, their enantiomers (e.g., non-natural amino acids), —$CH_2CN$, and a substituent having formula (II):

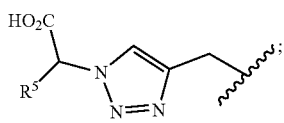

(II)

and $R^5$ is selected from the group consisting of side chains for genetically encoded amino acids and their enantiomers (e.g., non-natural amino acids).

In another aspect, the invention provides compounds having formula (IA)

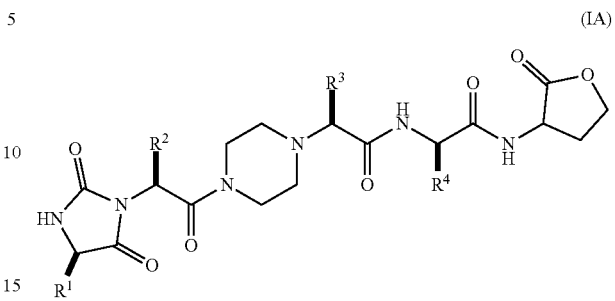

(IA)

or a stereoisomer or a pharmaceutically acceptable salt thereof, wherein $R^1$, $R^2$, $R^3$, and $R^4$ are independently selected from the group consisting of side chains for genetically encoded amino acids and their enantiomers (e.g., non-natural amino acids).

In a further aspect, the invention provides a compound having formula (IB)

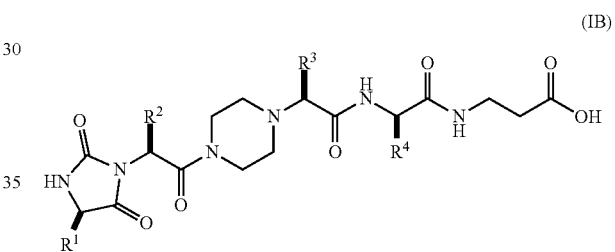

(IB)

or a stereoisomer or a pharmaceutically acceptable or ester salt thereof, wherein $R^1$, $R^2$, $R^3$, and $R^4$ are independently selected from the group consisting of side chains for genetically encoded amino acids, their enantiomers (e.g., non-natural amino acids), and —$CH_2CN$.

In an additional aspect, the invention provides a compound having formula (IC)

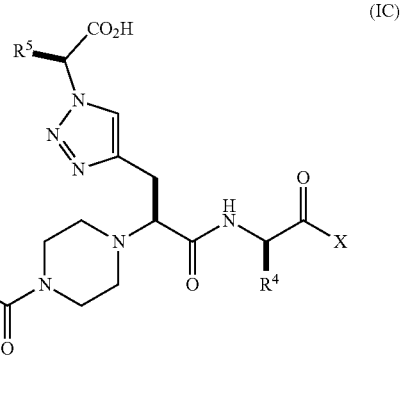

(IC)

or a stereoisomer or a pharmaceutically acceptable salt or ester thereof,
wherein
X is $NH_2$ or OH;

$R^1$, $R^2$, and $R^4$ are independently selected from the group consisting of side chains for genetically encoded amino acids, their enantiomers (e.g., non-natural amino acids), and —$CH_2CN$; and $R^5$ is selected from the group consisting of side chains for genetically encoded amino acids and their enantiomers (e.g., non-natural amino acids).

The heavy bonds in formulae (I), (IA), (IB), and (IC) represent bonds to asymmetric (chiral) carbons. Compounds of the invention include all possible stereoisomers of formulae (I), (IA), (IB), and (IC), including racemic mixtures, enantiomers, and diastereomers.

In certain embodiments, $R^1$ is an amino acid side chain selected from the group consisting of side chains of asparagine (—$CH_2CONH_2$), aspartic acid (—$CH_2CO_2H$), glutamine (—$CH_2CH_2CONH_2$), glutamic acid (—$CH_2CH_2CO_2H$), and valine (—$CH(CH_3)_2$). In some embodiments, $R^1$ is the amino acid side chain of asparagine or aspartic acid.

In certain embodiments, $R^2$ is an amino acid side chain selected from the group consisting of side chains of cysteine (—$CH_2SH$), asparagine (—$CH_2CONH_2$), and leucine (—$CH_2CH(CH_3)_2$). In some embodiments, $R^2$ is the amino acid side chain of leucine or cysteine.

In certain embodiments, $R^3$ is an amino acid side chain selected from the group consisting of side chains of asparagine (—$CH_2CONH_2$), aspartic acid (—$CH_2CO_2H$), and valine (—$CH(CH_3)_2$).

In certain embodiments, the invention includes compounds of formulae (I), (IA), and (IB), in which $R^3$ is —$CH_2CN$. In these embodiments, the side chain is not genetically encoded, and —$CH_2CN$ is the entire side chain.

In some embodiments, the invention includes compounds of formula (IC), wherein $R^5$ is a methyl, —$CH_2OH$, propyl, —$CH_2CH_2SCH_3$, —$CH_2CH_2CH_2CH_2NH_2$, —$CH_2CONH_2$, or a side chain of a basic amino acid (e.g., lysine, arginine histidine, tryptophan).

In some embodiments, $R^3$ is the amino acid side chain of asparagine, leucine, or $CH_2CN$. In certain embodiments, $R^3$ is the amino acid side chain of asparagine, In certain embodiments, $R^4$ is an amino acid side chain of a basic amino acid (i.e., an amino acid that becomes positively charged at acidic pH (e.g., lysine, arginine histidine, tryptophan). In certain embodiments, $R^4$ is an amino acid side chain selected from the group consisting of side chains of lysine (—$CH_2CH_2CH_2CH_2NH_2$), arginine (—$CH_2CH_2CH_2NHC(=NH)NH_2$), histidine (—$CH_2$—$C_3H_3N_2$), and tryptophan (—$CH_2$—$C_8H_6N$). In some embodiments, $R^4$ is the amino acid side chain of arginine.

In certain embodiments, combinations of $R^1$, $R^2$, $R^3$, and $R^4$ are the side chains from, respectively:
(1) aspartic acid, leucine, asparagine, arginine;
(2) aspartic acid, cysteine, leucine, arginine;
(3) asparagine, cysteine, leucine, lysine;
(4) aspartic acid, leucine, —$CH_2CN$*, arginine;
(5) glutamine, asparagine, aspartic acid, arginine; and
(6) glutamic acid, asparagine, aspartic acid, arginine.
*—$CH_2CN$ is the entire side chain ($R^3$) in this embodiment.

As used herein, the term "pharmaceutically acceptable salt or ester thereof" refers to a pharmaceutically acceptable salt or a pharmaceutically acceptable ester of a compound of formulae (I), (IA), (IB), or (IC).

In certain embodiments, the compounds of the invention are amine compounds. Pharmaceutically acceptable salts of these compounds include acid addition salts. Suitable pharmaceutically acceptable acid addition salts are known in the art. Representative pharmaceutically acceptable salts include HCl addition salts and $RCO_2H$ addition salts, where R is, for example, hydrogen, a substituted or unsubstituted C1-C8 alkyl, or a substituted or unsubstituted aryl group (e.g., phenyl). Representative pharmaceutically acceptable salts include benzoates, tosylates, mesylates, and besylates.

In other embodiments, the compounds of the invention are carboxy (—$CO_2H$) compounds. Pharmaceutically acceptable salts of these compounds are carboxylate (—$CO_2$—) salts having cationic (positively charged) counter ions. Suitable pharmaceutically acceptable carboxylate salts are known in the art. Representative pharmaceutically acceptable salts include potassium ($K^+$), sodium ($Na^+$) salts.

In certain embodiments, the compounds of the invention are carboxy (—$CO_2H$) compounds and for these compounds pharmaceutically acceptable esters are carboxylic acid esters (i.e., —$CO_2R$, where R is, for example, hydrogen, a substituted or unsubstituted C1-C8 alkyl, or a substituted or unsubstituted aryl group (e.g., phenyl)). Suitable pharmaceutically acceptable esters are known in the art. Representative pharmaceutically acceptable esters include methyl, ethyl, propyl, and phenyl esters.

Figure 4:
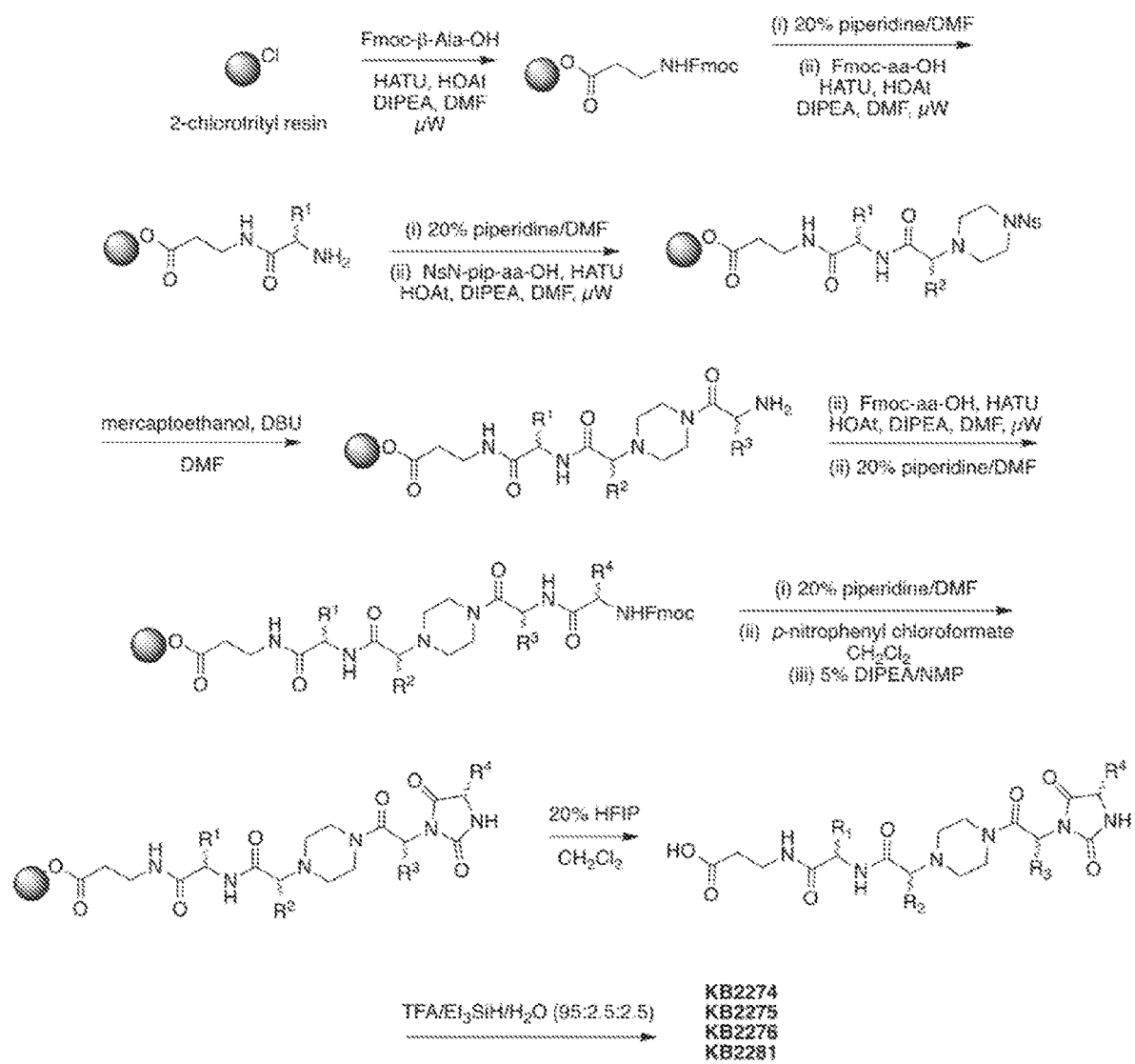
FIG. 4 is a schematic illustration of the preparation of representative compounds of the invention: solid phase syntheses of compounds having β-alanine C-terminus.
Figure 5:
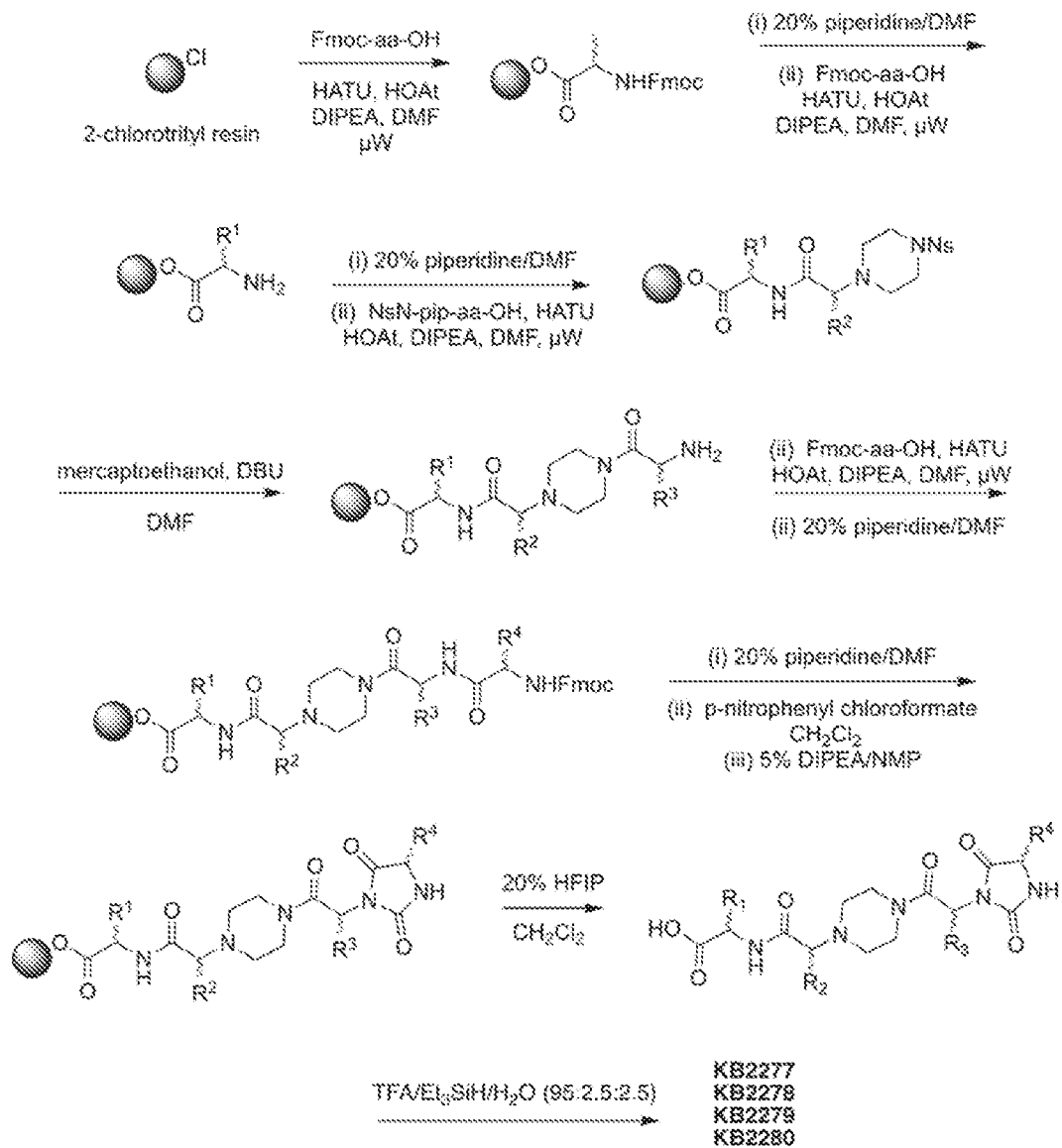
FIG. 5 is a schematic illustration of the preparation of representative compounds of the invention: solid phase syntheses of compounds with α-amino acid C-terminus.

Schematic illustrations of the preparation of representative compounds of the invention are shown in FIGS. 1, 4, and 5.

Figure 2:
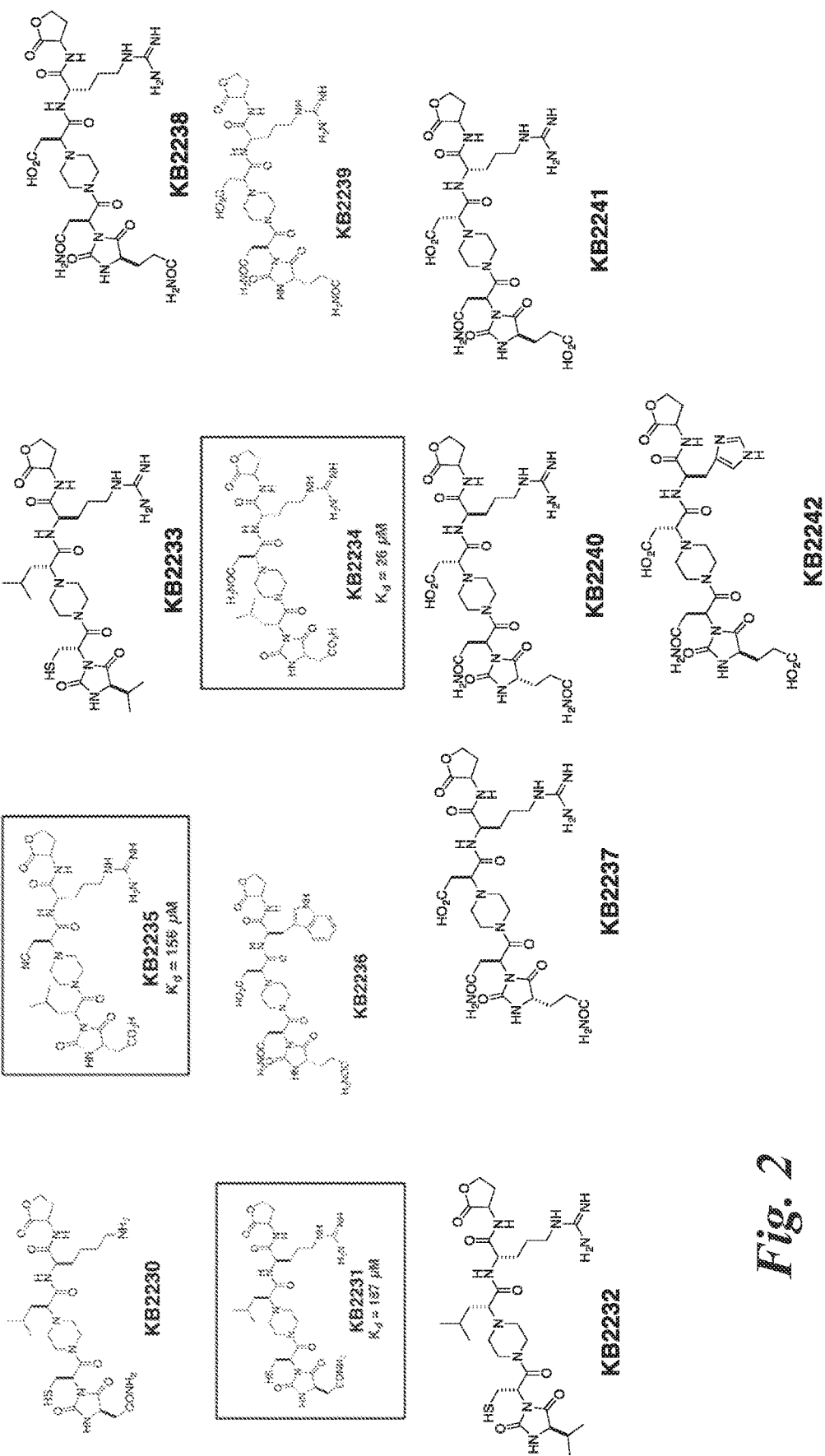
FIG. 2 illustrates the chemical structures of representative compounds of the invention.
Figure 6:
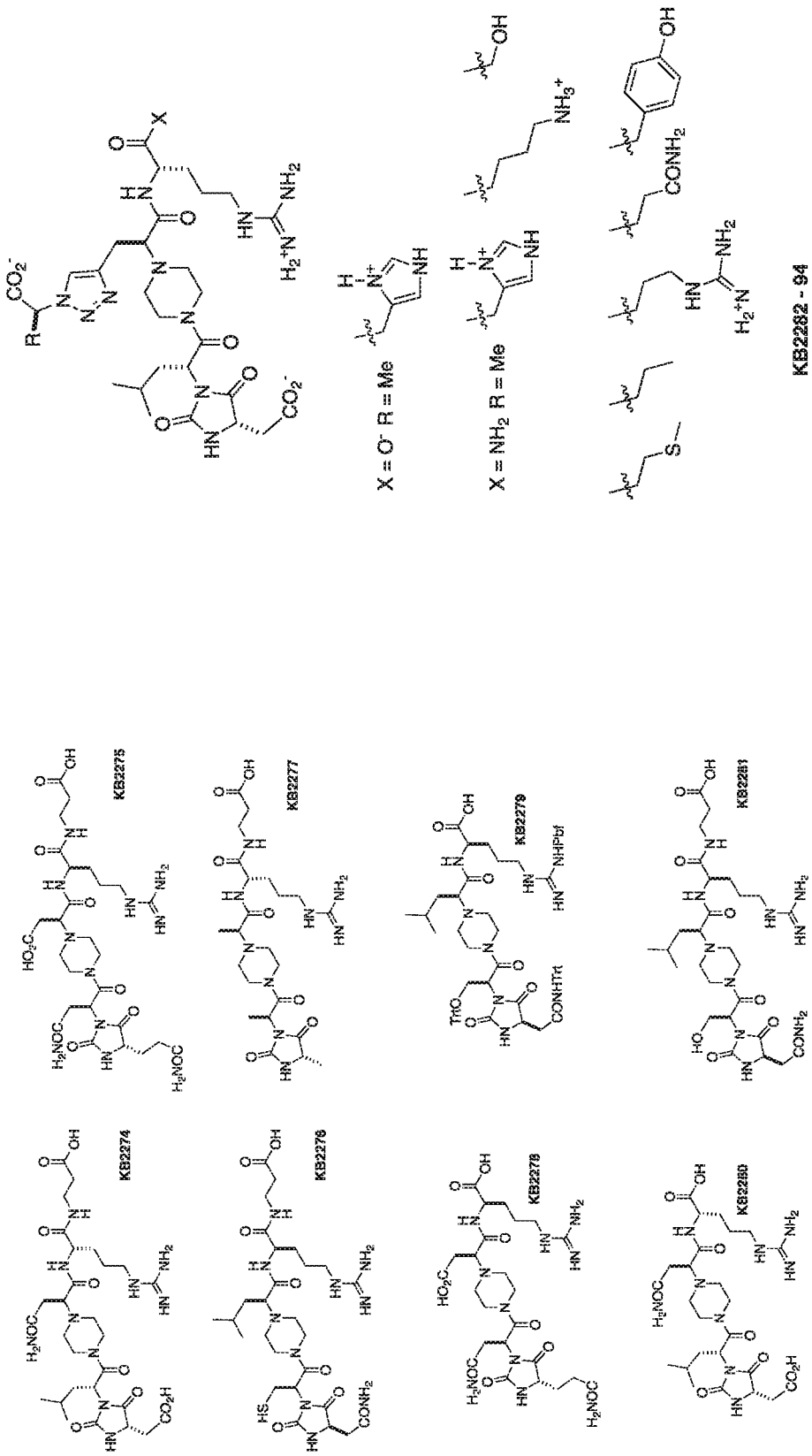
FIG. 6 illustrates the chemical structures of representative compounds of the invention.

Representative compounds of the invention are shown in FIG. 2 and FIG. 6.

Properties ($K_d$ (μm), LDL-uptake) of select representative compounds of the invention are summarized in FIG. 3. The Biocore experiments to obtain $K_D$ values were performed on a T200 instrument using direct coupling, and 5% DMSO and 2 mM $CaCl_2$ were included in TBS.

Assays for cellular uptake of fluorescently labeled LDL-C were performed in the following way. HepG2 cells were seeded into 96-well plate at a density of $3×10^4$ cells/well in DMEM/F12 medium (Sigma-Aldrich) for 24 h. After 24 h, the medium was aspirated and cells were washed two times with PBS. 10% Lipoprotein-deficient serum (Gemini) in DMEM was added and the cells were incubated for another 24 h. After 24 h, Pep2-8 (30 μM) or inhibitors at various concentrations (50, 5, 0.5 μM) was pre-incubated with 15 μg/mL PCSK9 in 10% lipoprotein-deficient/DMEM containing 0.5% DMSO for 30 min. Cells were aspirated and washed two times with PBS, then the test inhibitors were added and incubated for 2 h. BODIPY-LDL (10 μg/mL, Invitrogen) was added and incubated for another 3 h. Cells were washed three times with PBS, and fluorescence was measured on Synergy H4 plate reader (Biotek) with excitation and emission wavelength at 488 and 520 nm, respectively.

The preparation and characterization of representative compounds of the invention are described in the Examples.

The compounds of the invention (or stereoisomers or pharmaceutically acceptable salts or esters thereof) can in particular be used for treating any subject wherein blocking, inhibiting or neutralizing the in vivo effect of PCSK9 or blocking or inhibiting the interaction of PCSK9 and LDLR is therapeutically desirable (e.g., modulating PCSK9 activity). As used herein, the term "PCSK9 activity" includes any biological effect of PCSK9. In certain embodiments, PCSK9 activity is represented by the ability of PCSK9 to bind to a LDL-R receptor (LDLR). In some embodiments, PCSK9 activity includes the ability of PCSK9 to alter (e.g., reduce)

the availability of LDLR. In some embodiments, PCSK9 activity includes the ability of PCSK9 to increase the amount of LDL-C in a subject. In some embodiments, PCSK9 activity includes the ability of PCSK9 to decrease the amount of LDLR that is available to bind to LDL. In some embodiments, PCSK9 activity includes any biological activity resulting from PCSK9 signaling. Exemplary activities include PCSK9 binding to LDLR, PCSK9 enzyme activity that cleaves LDLR or other proteins, and PCSK9 binding to proteins other than LDLR that facilitate PCSK9 action.

The compounds of the invention (or stereoisomers or pharmaceutically acceptable salts or esters thereof) can also in particular be used for treating or preventing disorders of cholesterol or lipid homeostasis and disorders, or complications associated therewith, which may be associated therewith including hypercholesterolemia, hyperlipidemia, hypertriglyceridaemia, sitosterolemia, atherosclerosis, arteriosclerosis, coronary heart disease, metabolic syndrome, acute coronary syndrome, vascular inflammation, diabetes, obesity, angina, hypertension and xanthoma by the administration of the compounds of the invention.

The term "hypercholesterolemia," as used herein, refers to a condition in which cholesterol levels are elevated above a desired level. In some embodiments, this denotes that serum cholesterol levels are elevated. In some embodiments, the desired level takes into account various "risk factors" that are known to one of skill in the art (and are described or referenced herein).

The compounds of the invention (or stereoisomers or pharmaceutically acceptable salts or esters thereof) can also in particular be used for treating any subject having a condition or at risk of developing a condition wherein modulation of lipid or cholesterol levels is clinically desirable or where the subject has a condition that is often associated with high lipids or cholesterol.

The invention further relates to compositions containing a compound of the invention (or stereoisomer or pharmaceutically acceptable salt or ester thereof), especially compositions are suitable for in vivo administration (e.g., subcutaneous, intravenous, intradermal, intranasal, intrathecal, vaginal, rectal, and other injectable or topical administrable dosage forms). More specifically, the invention provides compositions containing a compound of the invention, or stereoisomer or pharmaceutically acceptable salt or ester thereof, especially compositions which are suitable for in vivo administration, e.g., subcutaneous, intravenous, intradermal, intranasal, intrathecal, vaginal, rectal, oral and other injectable or topical dosage forms, which optionally may contain another active agent such as statins, ACE inhibitors, angiotensin II receptor blockers (ARBs), antiarrhythmics, antiplatelet drugs, anti-clotting agents, diuretics, heart failure drugs, vasodilators, blood thinners, other anti-cholesterol drugs, and other drugs used to treat conditions wherein the treated individual may have high cholesterol.

In some aspects, the invention comprises a method for treating or preventing a condition associated with elevated serum cholesterol levels in a subject, the method comprising administering to a subject in need thereof an effective amount of a compound of the invention, or stereoisomer or pharmaceutically acceptable salt or ester thereof.

In some aspects, the invention comprises a method of lowering serum cholesterol levels in a subject, the method comprising administering to a subject an effective amount of a compound of the invention, or stereoisomer or pharmaceutically acceptable salt or ester thereof.

In some aspects, the invention comprises a method of increasing LDLR protein level in a subject, the method comprising administering to a subject an effective amount of a compound of the invention, or stereoisomer or pharmaceutically acceptable salt or ester thereof.

In other aspects, the present invention provides methods for treating or preventing disorders of cholesterol or lipid homeostasis and disorders and complications associated therewith (e.g., hypercholesterolemia, hyperlipidemia, hypertriglyceridaemia, sitosterolemia, atherosclerosis, arteriosclerosis, coronary heart disease, metabolic syndrome, acute coronary syndrome, vascular inflammation, xanthoma and related conditions) using a compound of the invention, or stereoisomer or pharmaceutically acceptable salt or ester thereof.

In some aspects, the invention comprises a pharmaceutical composition comprising a compound of the invention, or stereoisomer or pharmaceutically acceptable salt or ester thereof, and a pharmaceutically acceptable carrier.

The following examples are provided for the purpose of illustrating, not limiting the invention.

EXAMPLES

A. General Procedure for the Preparation of Representative Compounds

The following is a description of the preparation of representative compounds of the invention. A synthetic procedure for making compounds of the invention is illustrated schematically in FIG. 1.

Fmoc Amino Acids Coupling

For any amino acids except cysteine, histidine and arginine, 4 equiv. of Fmoc protected amino acid, 8 equiv. of DIPEA were dissolved in 0.2 M HATU/HOAt in DMF. The mixture was added to the beads. Beads were stirred under microwave irradiation (MARS, CEM) at 75° C. for 10 min. Beads were washed 5 times with DMF.

For cysteine and histidine residues, beads were irradiated at 50° C. for 15 min instead.

For arginine residue, beads were shaken at room temperature for 20 min before irradiated at 75° C. for 10 min. Then, the solution was discarded; the fresh solution was added and irradiated at 75° C. for another 10 min.

Fmoc Deprotection Procedure

Fmoc group was deprotected in 20% piperidine/DMF under microwave irradiation (75° C., 3 min). Beads were washed thoroughly with DMF 5 times, MeOH 3 times, $CH_2Cl_2$ 3 times and DMF 3 times.

Syntheses on Solid Support

Tentagel S $NH_2$ beads were swollen in $CH_2Cl_2$ and DMF for 15 min and 1 h, respectively. Beads were loaded with Fmoc-methionine residue according to the general procedure of Fmoc amino acids coupling described above. Beads were washed with DMF and the Fmoc group was deprotected in 20% piperidine/DMF as described above. The procedure was repeated to couple another amino acids ($R^4$). The nosyl-piperazine amino acid ($R^3$) was coupled similar to the Fmoc-amino acids protocol. The nosyl protecting group was removed by mixing beads with the solution of 5 equiv. mercaptoethanol/DBU in DMF at 0.25 M at room temperature for 15 min. Solution was drained and the deprotection was repeated again with fresh mercaptoethanol/DBU solution. Complete nosyl deprotection can be monitored by chloranil test. Two Fmoc-amino acids ($R^1$, $R^2$) were coupled/deprotected to obtain linear peptides ($R^1$-$R^4$). After Fmoc deprotection, the solution of 3 equiv. p-nitrophenyl chloroformate and 6 equiv. DIPEA in MeCN at 0.06 M concentration was added and the beads were shaken at room temperature for 30 min twice. After draining and washing with MeCN and NMP, beads were shaken in 5% DIPEA/NMP 5 times for 30 min each. Beads were thoroughly washed with NMP, $CH_2Cl_2$ and MeOH before cleavage.

Cleavage, Purification and Side-Chain Deprotection

Beads were treated with the solution of 30 mg/mL cyanogen bromide in 5:4:1 MeCN/AcOH/water cocktail for at least 24 h. Solution was collected, dried and purified by preparative RP-HPLC (150×12.2 mm C-18 column using 50-95% acetonitrile with water gradient conditions, flow rate 7 mL/min). Compounds were lyophilized to get the side-chain protected KB compounds. These compounds were treated with 95:2.5:2.5 TFA/Et$_3$SiH/water solution for 3 h. Solution was evaporated and azeotroped several times with $CH_2Cl_2$. Products were precipitated in cold diethyl ether and washed several times with diethyl ether. Compounds were dissolved in water and lyophilized to remove any trace of solvent to obtain lyophilized powder. Purity was monitored using RP-LCMS (Agilent technologies, 4.6×50 mm RP Poroshell 120 EC-C18 2.7 µm, flow rate 0.5 mL/min with 5-95% acetonitrile/water gradient conditions) with UV detection at 220 nm.

Examples 1-13 present the characterization of representative compounds of the invention prepared as described above.

Example 1: KB2230

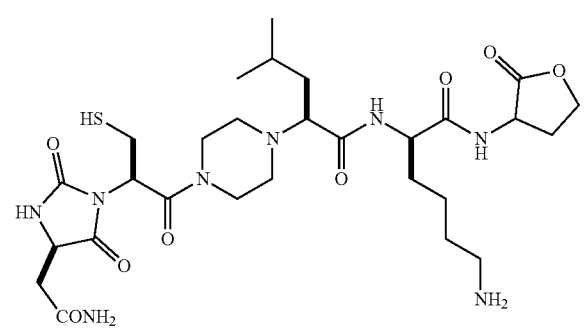 [SMILES: CC(C)C[C@@H](C(=O)N[C@H](CCCCN)C(=O)NC1CCOC1=O)N1CCN(C(=O)[C@H](CS)N2C(=O)N[C@H](CC(N)=O)C2=O)CC1]

KB2230; $t_R$=3.9 min, MS (ESI+) m/z calcd for $C_{28}H_{47}N_8O_8S$ (M+H)$^+$ 654.3; found 655.1.

Example 2: KB2231

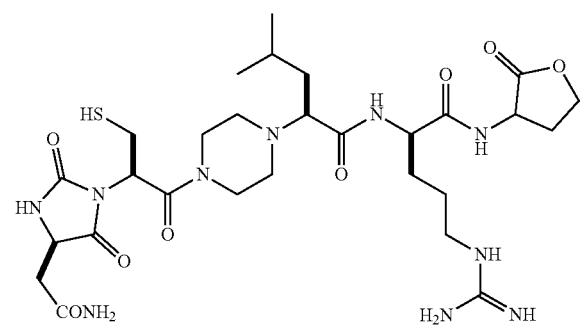 [SMILES: CC(C)C[C@@H](C(=O)N[C@H](CCCNC(=N)N)C(=O)NC1CCOC1=O)N1CCN(C(=O)[C@H](CS)N2C(=O)N[C@H](CC(N)=O)C2=O)CC1]

KB2231; $t_R$=4.0 min, MS (ESI+) m/z calcd for $C_{28}H_{47}N_{10}O_8S$ (M+H)$^+$ 682.3; found 682.6.

Example 3: KB2232

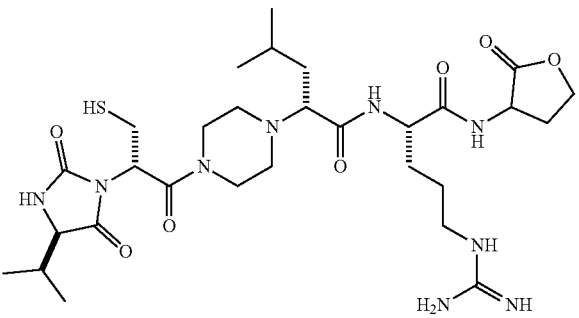 [SMILES: CC(C)C[C@H](C(=O)N[C@@H](CCCNC(=N)N)C(=O)NC1CCOC1=O)N1CCN(C(=O)[C@@H](CS)N2C(=O)N[C@H](C(C)C)C2=O)CC1]

KB2232; $t_R$=4.7 min, MS (ESI+) m/z calcd for $C_{29}H_{50}N_9O_7S$ (M+H)$^+$ 667.3; found 668.2.

Example 4: KB2233

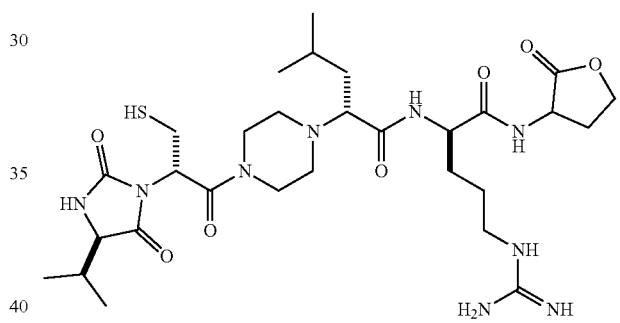

KB2233; $t_R$=4.8 min, MS (ESI+) m/z calcd for $C_{29}H_{50}N_9O_7S$ (M+H)$^+$ 667.3; found 668.2.

Example 5: KB2234

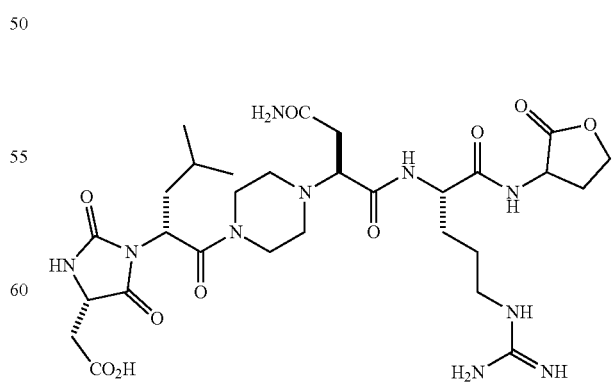

KB2234; $t_R$=4.4 min, MS (ESI+) m/z calcd for $C_{29}H_{47}N_{10}O_{10}$ (M+H)$^+$ 694.3; found 695.2.

Example 6: KB2235

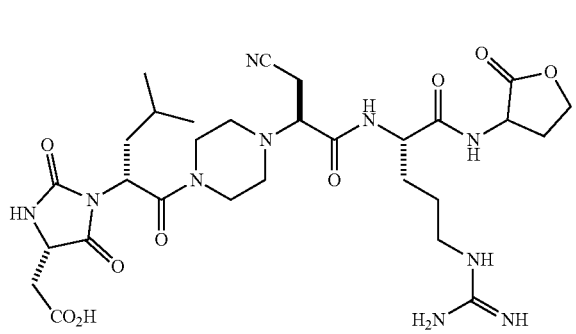 [SMILES: CC(C)C[C@H](C(=O)N1CCN([C@@H](CC#N)C(=O)N[C@@H](CCCNC(=N)N)C(=O)NC2CCOC2=O)CC1)N1C(=O)N[C@@H](CC(=O)O)C1=O]

KB2235; $t_R$=4.7 min, MS (ESI+) m/z calcd for $C_{29}H_{45}N_{10}O_9$ (M+H)$^+$ 676.3; found 677.2.

Example 7: KB2236

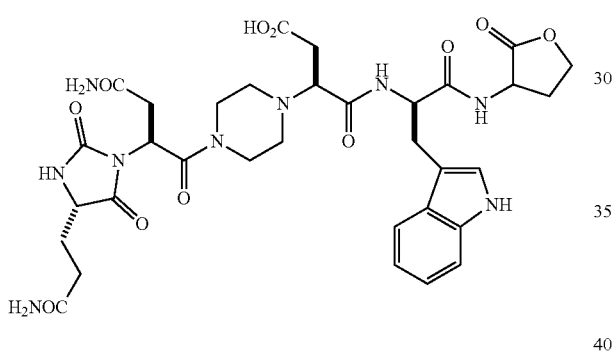

KB2236; $t_R$=4.6 min, MS (ESI+) m/z calcd for $C_{33}H_{42}N_9O_{11}$ (M+H)$^+$ 739.3; found 740.1.

Example 8: KB2237

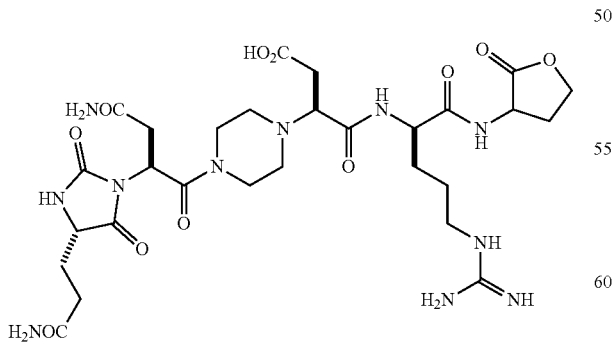

KB2237; $t_R$=1.4 min, MS (ESI+) m/z calcd for $C_{28}H_{44}N_{11}O_{11}$ (M+H)$^+$ 709.3; found 710.1.

Example 9: KB2238

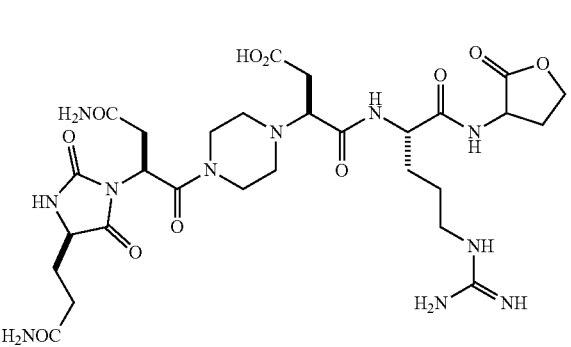 [SMILES: N=C(N)NCCC[C@H](NC(=O)[C@H](CC(=O)O)N1CCN(C(=O)[C@H](CC(N)=O)N2C(=O)N[C@H](CCC(N)=O)C2=O)CC1)C(=O)NC1CCOC1=O]

KB2238; $t_R$=1.4 min, MS (ESI+) m/z calcd for $C_{28}H_{44}N_{11}O_{11}$ (M+H)$^+$ 709.3; found 710.1.

Example 10: KB2239

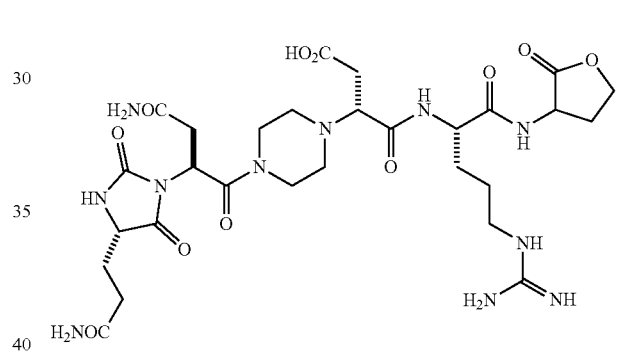

KB2239; $t_R$=1.4 min, MS (ESI+) m/z calcd for $C_{28}H_{44}N_{11}O_{11}$ (M+H)$^+$ 709.3; found 710.1.

Example 11: KB2240

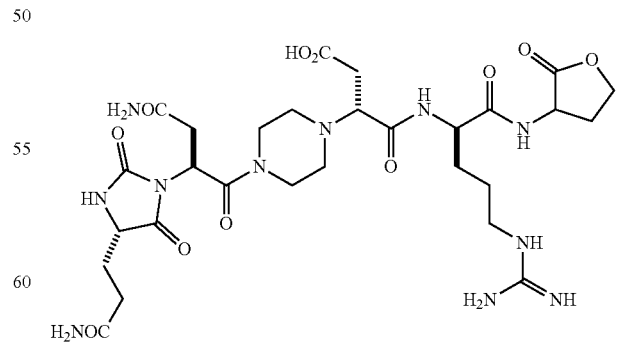

KB2240; $t_R$=1.4 min, MS (ESI+) m/z calcd for $C_{28}H_{44}N_{11}O_{11}$ (M+H)$^+$ 709.3; found 710.1.

Example 12: KB2241

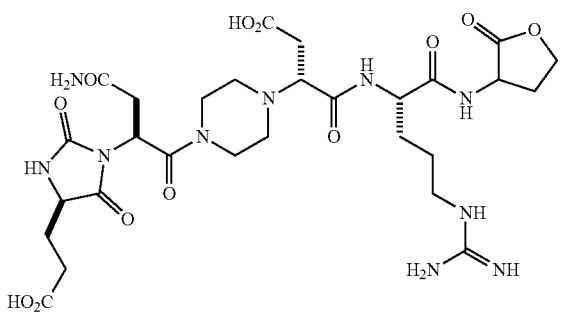 [SMILES: N=C(N)NCCC[C@H](NC(=O)[C@@H](CC(=O)O)N1CCN(C(=O)[C@H](CC(N)=O)N2C(=O)N[C@H](CCC(=O)O)C2=O)CC1)C(=O)NC1CCOC1=O]

KB2241; $t_R$=1.4 min, MS (ESI+) m/z calcd for $C_{28}H_{43}N_{10}O_{12}$ (M+H)$^+$ 710.3; found 711.2.

Example 13: KB2242

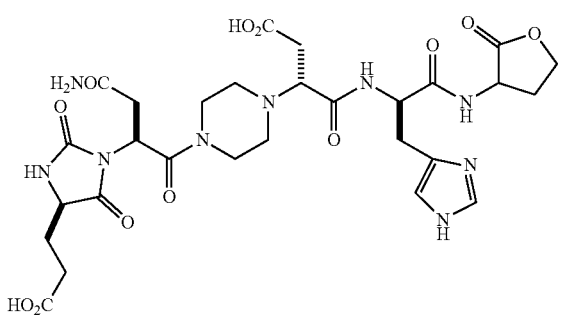 [SMILES: NC(=O)C[C@@H](C(=O)N1CCN([C@H](CC(=O)O)C(=O)N[C@H](Cc2c[nH]cn2)C(=O)NC2CCOC2=O)CC1)N1C(=O)N[C@H](CCC(=O)O)C1=O]

KB2242; $t_R$=1.4 min, MS (ESI+) m/z calcd for $C_{28}H_{38}N_9O_{12}$ (M+H)$^+$ 691.3; found 692.1.

B. Alternative Synthetic Procedure for Solid Phase Synthesis of Representative Compound Representative synthetic procedures for making compounds of the invention are illustrated schematically in FIGS. 4 and 5.

Cl-Trt resin (500 mg, 1.2 meq/g) was shaken with anhydrous CH$_2$Cl$_2$ (5 mL) in a fritted syringe for 1 hr. CH$_2$Cl$_2$ was then drained and the resin was allowed to further swell in anhydrous DMF (6 mL) for another 30 min. The solvent was again drained out and a mixture of the first amino acid (β-alanine, L-arginine, or D-arginine) (224 mg, 0.6 mmol) and $^i$Pr$_2$NEt (1.5 mL) in DMF (1.5 mL) was added into the syringe and the reaction was carried out at 50° C. in a microwave-assisted peptide synthesizer for 30 min. The remaining reactive site was blocked with MeOH/Pr$_2$NEt (9:1 v/v) for 1 hour at room temperature and the beads were washed with DMF 5 times.

For the coupling reactions, 100 mg of the loaded resin, 4 equiv. of Fmoc amino acid or Nosyl-protected Pip-acid, 4 equiv. of HATU, 4 equiv. of HOAt, and 4 equiv. of $^i$Pr$_2$NEt were used at 0.2 M concentration in DMF. in a microwave-assisted peptide synthesizer for 15 min at 50° C. The beads were washed with DMF 5 times after the coupling reaction and a few beads were subjected to Kaiser test to confirm the completion of the coupling reaction.

Fmoc groups were deprotected by treating the beads with 20% piperidine in DMF at 75° C. in a microwave-assisted peptide synthesizer for 3 min. The beads were washed with DMF 5 times, CH$_2$Cl$_2$ 3 times, and again with DMF 3 times after the treatment. A few beads were subjected to Kaiser test to confirm the completion of the deprotection reaction.

Nosyl deprotection was done using 5 equiv of DBU and 5 equiv of mercaptoethanol in DMF at 0.2 M concentration. The beads were allowed to shake at room temperature for 30 min. The solution was drained completely and the beads were washed with DMF three times. The deprotection was repeated with fresh reagents to ensure completion. The beads were washed similar to the Fmoc deprotection procedure. A few beads were subjected to Chloranil test to confirm the completion of the deprotection reaction.

For the hydantoin cyclization, the beads were washed three time with CH$_2$Cl$_2$ prior to the addition of as 3 equiv of p-nitrophenyl chloroformate and 6 equiv of diisopropylethylamine in CH$_2$Cl$_2$ at 0.05 M concentration. The beads were allowed to shake at room temperature for 1 hr. The solution was then drained, the beads were washed with CH$_2$Cl$_2$, and the procedure was repeated with fresh reagents to ensure completion. The beads were washed similar to the Fmoc deprotection but with N-methyl-2-pyrrolidone (NMP) at the end. The beads were further shaken with 5% di-iso-propylethylamine in NMP at room temperature for 30 min, at least seven times, to wash off the side products. The beads were washed for a final time with 5 times each with CH$_2$Cl$_2$, DMF, and MeOH.

The peptides were then cleaved off from the solid support by treating the beads with HFIP/CH$_2$Cl$_2$ (1:4 v/v, 15 mL/g beads) for 8 hr at room temperature. After filtration, the beads were washed with CH$_2$Cl$_2$ and the combined organic solvents were removed under vacuum and the crude material was dried under high vacuum to give the crude product. The crude material was purified by Prep HPLC using a reverse phase C18 column and gradients of acetonitrile in water. The fully protected products can now either be subjected to further modification or deprotected by TFA/Et$_3$SiH/H$_2$O (95:2.5:2.5).

Examples 14 and 15 present the characterization of representative compounds of the invention prepared as described above by Procedure B.

Example 14: KB2274

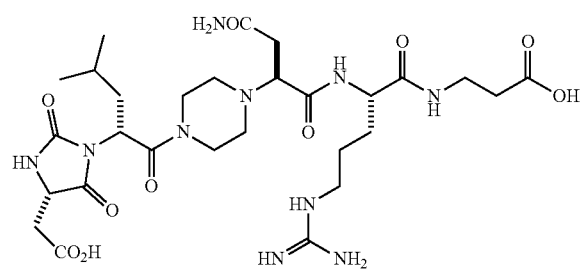 [SMILES: CC(C)C[C@H](C(=O)N1CCN([C@@H](CC(N)=O)C(=O)N[C@@H](CCCNC(=N)N)C(=O)NCCC(=O)O)CC1)N1C(=O)N[C@@H](CC(=O)O)C1=O]

KB2274: Solid phase synthesis was done using 100 mg of loaded Cl-Trt resin following the general synthetic procedure yielding 14.1 mg as a white solid. $^1$H NMR (400 MHz, DMSO-d$_6$) δ 8.31 (s, 1H), 8.20 (d, J=8.1 Hz, 1H), 7.95 (dd, J=5.3, 9.6 Hz, 1H), 7.71 (bs, 1H), 7.47 (s, 1H), 7.12 (bs, 2H), 6.88 (s, 1H), 4.68 (dd, J=4.4, 9.6 Hz, 1H), 4.22 (t, J=4.9 Hz, 1H), 4.16 (m, 1H), 3.60 (t, J=7.8 Hz, 2H), 3.32 (m, 4H), 3.09 (dd, J 5.7, 10.5 Hz, 2H), 3.08 (s, 1H), 2.64 (m, 2H), 2.54 (m, 1H), 2.36 (m, 5H), 2.05 (m, 1H), 1.76 (m, 1H), 0.87 (dd, J=6.9, 8.3 Hz, 6H). $^{13}$C (100 MHz, DMSO-d$_6$) δ 173.3, 172.9, 172.7, 171.2, 170.9. 170.0, 166.5, 156.8, 156.4, 63.3, 52.8, 52.1, 49.1, 36.6, 33.7, 33.6, 28.8, 26.8, 25.1, 24.0, 23.0, 21.3. HRMS (ESI) calcd for $C_{28}H_{46}N_{10}O_{10}$ [M+H] 682.7440, found 683.3459.

Example 15: KB2275

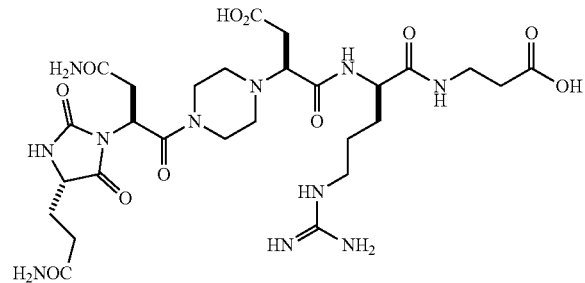 [SMILES: N=C(N)NCCC[C@@H](NC(=O)[C@H](CC(=O)O)N1CCN(C(=O)[C@H](CC(N)=O)N2C(=O)N[C@@H](CCC(N)=O)C2=O)CC1)C(=O)NCCC(=O)O]

KB2275: Solid phase synthesis was done using 100 mg of loaded Cl-Trt resin following the general synthetic procedure yielding 15.3 mg as a white solid. $^1$H NMR (400 MHz, DMSO-$d_6$) δ 8.32 (s, 1H), 8.01 (d, J=8.4 Hz, 2H), 7.67 (dt, J 5.6, 16.9 Hz, 1H), 7.44 (s, 1H), 7.29 (s, 2H), 7.12 (bs, 2H), 6.82 (s, 1H), 6.78 (s, 1H), 5.10 (t, J=7.3 Hz, 1H), 4.24 (dd, J=8.6, 12.6 Hz, 2H), 4.08 (t, J=5.3 Hz, 2H), 3.93 (s, 1H), 3.66 (dd, J 5.4, 8.2 Hz, 2H), 3.40 (m, 4H), 3.08 (dd, J=7.6, 13.4 Hz, 2H), 2.88 (dd, J=7.0, 15.3 Hz, 1H), 2.71 (bs, 1H), 2.66 (dd, J=6.9, 15.1 Hz, 2H), 2.55 (dd, J=9.1, 15.1 Hz, 1H), 2.39 (m, 6H), 2.17 (t, J=7.7 Hz, 2H), 1.90 (m, 1H), 1.76 (q, J=6.9 Hz, 1H), 1.67 (m, 1H), 1.54 (m, 1H), 1.44 (m, 1H). $^{13}$C (100 MHz, DMSO-$d_6$) δ 174.0, 173.7, 173.4, 173.3, 171.7, 171.6, 170.4, 166.3, 157.2, 156.1, 64.0, 55.9, 52.2, 49.3, 47.7, 40.8, 35.3, 34.6, 34.2, 30.4, 31.2, 30.0, 28.0, 27.9, 25.2. HRMS (ESI) calcd for $C_{27}H_{43}N_{11}O_{11}$ [M+H] 698.7150, found 698.32088.

LDL Uptake for Representative Compounds
Procedure.

LDL-uptake assay was performed in quintuplicate following a published procedure with some modifications. HepG2 cells were seeded into 96-well plate at a density of $3 \times 10^4$ cells/well in DMEM with 10% FBS medium (Sigma-Aldrich). After a period of 24 h, the medium was aspirated and cells were washed with PBS twice. Cells were treated with 10% lipoprotein-deficient serum (Gemini) in DMEM and incubated for another 24 h. After washing cells with PBS twice, cells were incubated 2 h with either 100 μL of Pep2-8 (30 μM), inhibitors at various concentrations (50 μM), or negative control (DMSO), which were preincubated with 10 μg/mL PCSK9 in 10% lipoprotein-deficient DMEM at 0.5% DMSO level for 30 min prior. A positive control was also performed, in a similar fashion but in the absence of PCSK9. BODIPY-LDL (10 μg/mL, Invitrogen) was added to each well and cells were incubated for another 3 h. Cells were washed three times with PBS, and fluorescent intensity was measured on Synergy H4 plate reader (Biotek) with excitation and emission wavelength at 488 and 520 nm, respectively.

Results.

Figure 7:
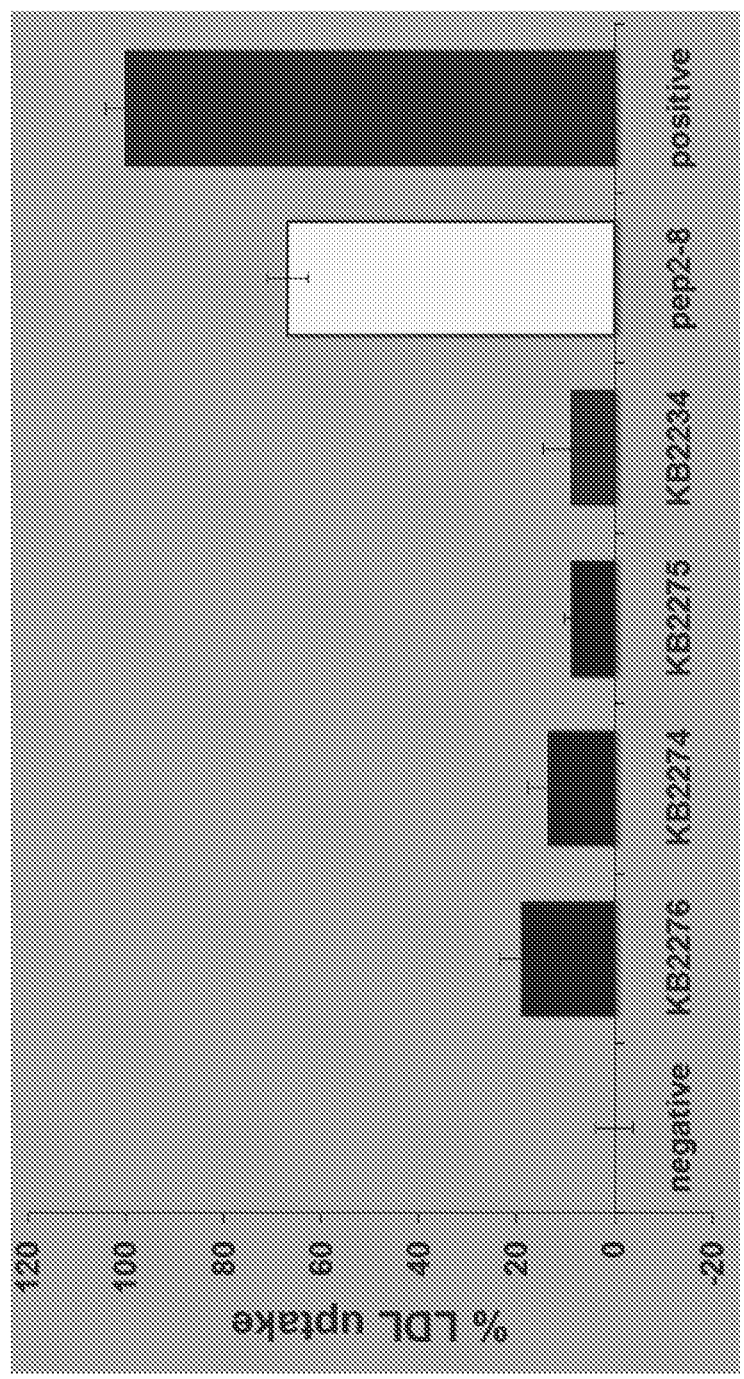
FIG. 7 summarizes illustrative data for LDL uptake assay of representative compounds of the invention.

Illustrative data for some of the compounds of the invention are shown in FIG. 7 and are summarized in Table 1. A similar % LDL uptake for all of the tested compounds as compared to the lead compound KB2234 was observed.

TABLE 1

| LDL uptake assay results | | |
|---|---|---|
| Compound | Mimic | % LDL uptake at 50 μM |
| KB2274 | LDLL-dlnr-βa | 13.5 ± 4.3 |
| KB2275 | LLLD-qndr-βa | 8.6 ± 1.5 |
| KB2276 | DLLD-nclr-βa | 19.0 ± 4.7 |
| KB2234 | DLLD-nclr-βa | 8.7 ± 5.9 |
| Pep2-8 | — | 66.9 ± 4.2 |

While the preferred embodiment of the invention has been illustrated and described, it will be appreciated that various changes can be made therein without departing from the spirit and scope of the invention.

The invention claimed is:

1. A compound having formula (I)

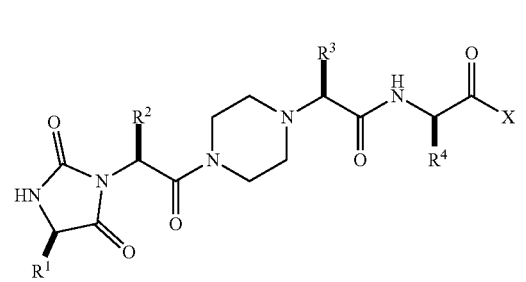

or a stereoisomer or a pharmaceutically acceptable salt thereof, wherein

X is selected from $NH_2$, OH, $NH(CH_2)_nCO_2H$, where n is an integer from 1 to 8, and

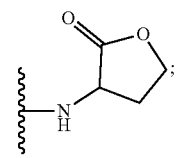

$R_1$, $R_2$, and $R_4$ are independently selected from the group consisting of side chains for genetically encoded amino acids, their enantiomers, and —$CH_2CN$; and $R_3$ is selected from the group consisting of side chains for genetically encoded amino acids, their enantiomers, —$CH_2CN$, and a substituent having formula (II):

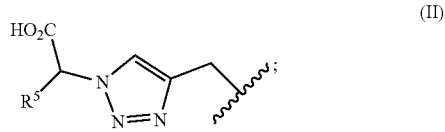

and $R_5$ is selected from the group consisting of side chains for genetically encoded amino acids and their enantiomers.

2. A compound of claim 1 having formula (IA)

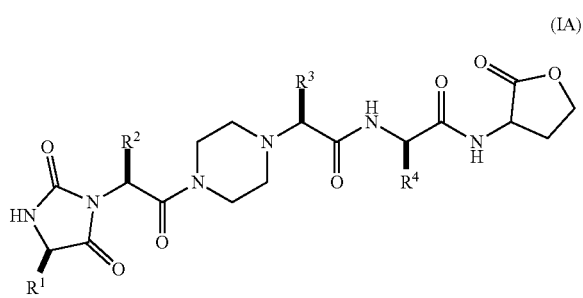

or a stereoisomer or a pharmaceutically acceptable salt thereof,
wherein
$R_1$, $R_2$, $R_3$, and $R_4$ are independently selected from the group consisting of side chains for genetically encoded amino acids, their enantiomers and —$CH_2CN$.

3. A compound of claim 1 having formula (IB)

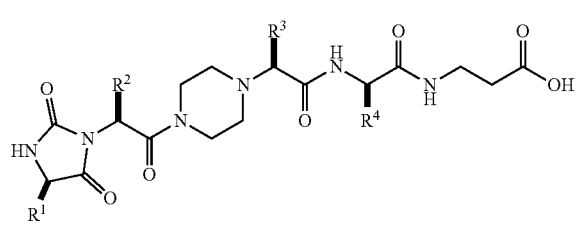

or a stereoisomer or a pharmaceutically acceptable salt thereof,
wherein
$R_1$, $R_2$, $R_3$, and $R_4$ are independently selected from the group consisting of side chains for genetically encoded amino acids, their enantiomers, and —$CH_2CN$.

4. The compound of claim 1, wherein $R_1$ is an amino acid side chain selected from the group consisting of side chains of asparagine (—$CH_2CONH_2$), aspartic acid (—$CH_2CO_2H$), glutamine (—$CH_2CH_2CONH_2$), glutamic acid (—$CH_2CH_2CO_2H$), and valine (—$CH(CH_3)_2$).

5. The compound of claim 1, wherein $R_1$ is the amino acid side chain of aspargine or aspartic acid.

6. The compound of claim 1, wherein $R_2$ is an amino acid side chain selected from the group consisting of side chains of cysteine (—$CH_2SH$), asparagine (—$CH_2CONH_2$), and leucine (—$CH_2CH(CH_3)_2$).

7. The compound of claim 1, wherein $R_2$ is the amino acid side chain of leucine or cysteine.

8. The compound of claim 1, wherein $R_3$ is an amino acid side chain selected from the group consisting of side chains of asparagine (—$CH_2CONH_2$), aspartic acid (—$CH_2CO_2H$), and valine (—$CH(CH_3)_2$).

9. The compound of claim 1, wherein $R_3$ is —$CH_2CN$.

10. The compound of claim 1, wherein $R_3$ is the amino acid side chain of asparagine, leucine, or —$CH_2CN$.

11. The compound of claim 1, wherein $R_4$ is an amino acid side chain selected from the group consisting of side chains of lysine (—$CH_2CH_2CH_2CH_2NH_2$), arginine (—$CH_2CH_2CH_2NHC(=NH)NH_2$), histidine (—$CH_2$—$C_3H_3N_2$), and tryptophan (—$CH_2$—$C_8H_6N$).

12. The compound of claim 1, wherein $R_4$ is the amino acid side chain of arginine.

13. A compound of claim 1 having formula (IC)

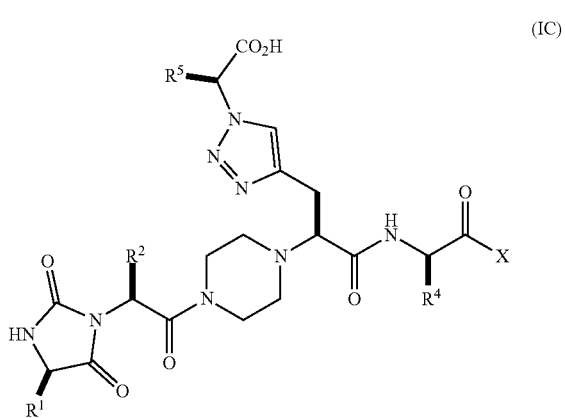

or a stereoisomer or a pharmaceutically acceptable salt thereof,
wherein
X is $NH_2$ or OH;
$R_1$, $R_2$, and $R_4$ are independently selected from the group consisting of side chains for genetically encoded amino acids, their enantiomers, and —$CH_2CN$; and
$R_5$ is selected from the group consisting of side chains for genetically encoded amino acids and their enantiomers.

14. A compound of claim 1 selected from the group consisting of:

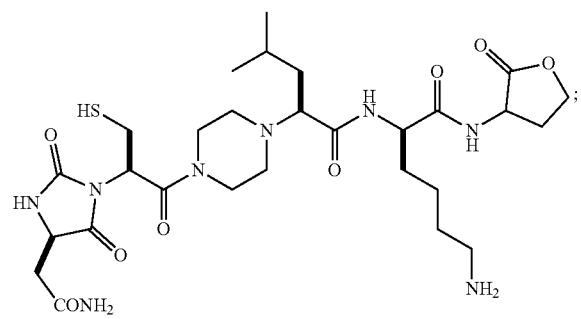

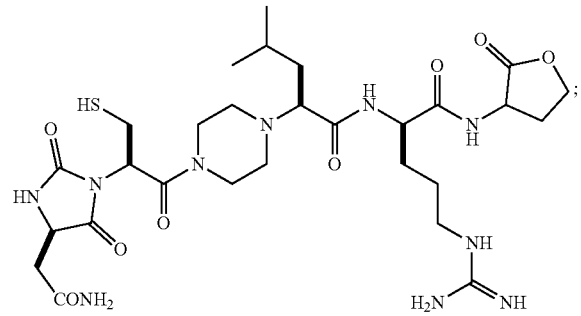

KB2232
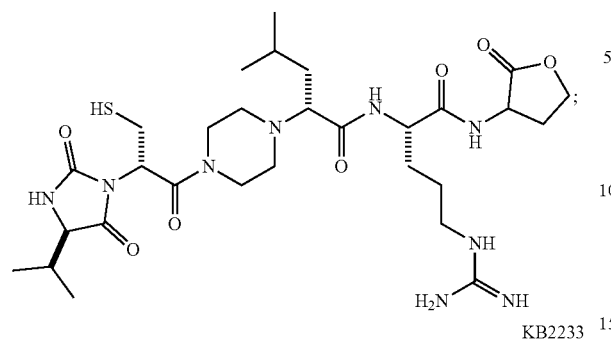
KB2237
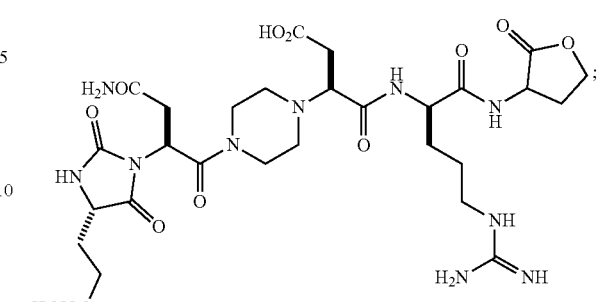
KB2233
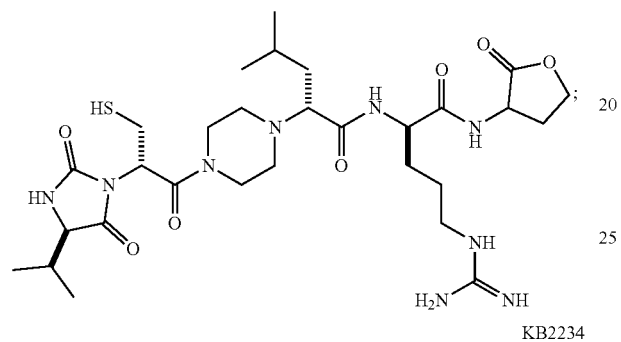
KB2238
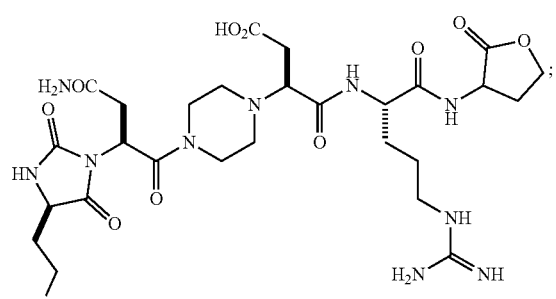
KB2234
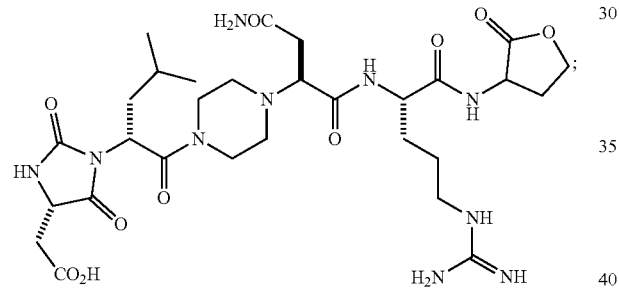
KB2239
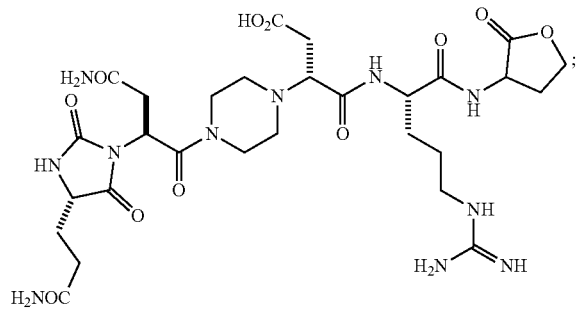
KB2235
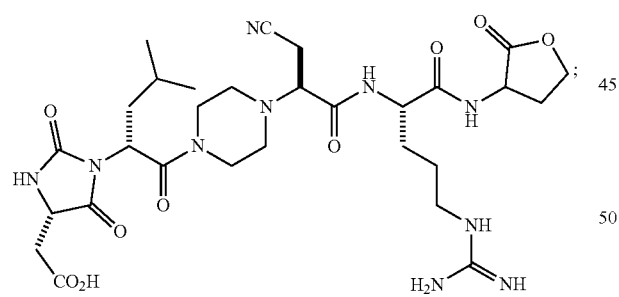
KB2240
KB2236
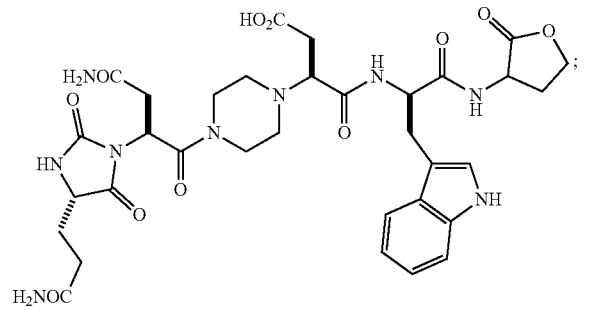

-continued
KB2241
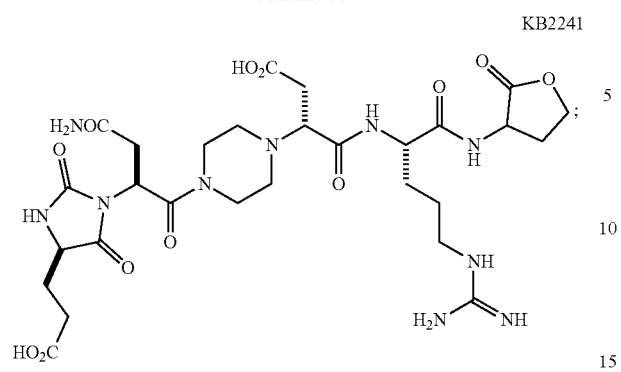
KB2242
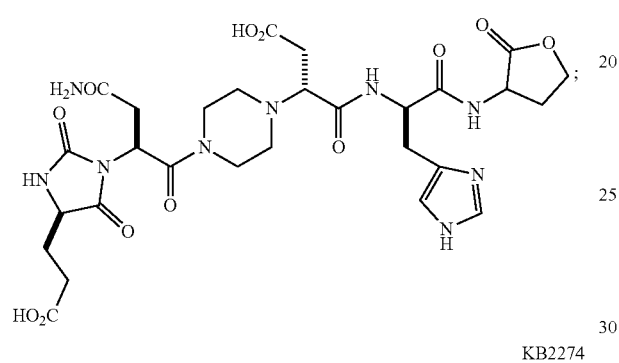
KB2274
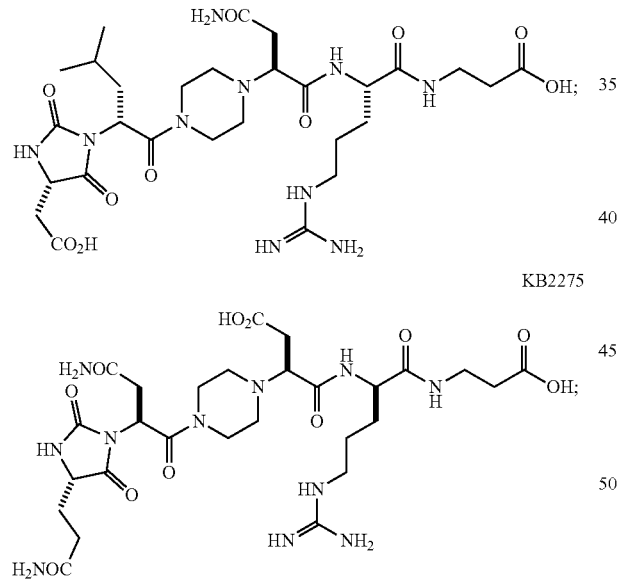
KB2275
KB2276
KB2277
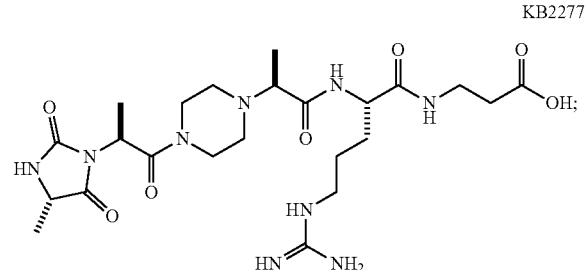
KB2278
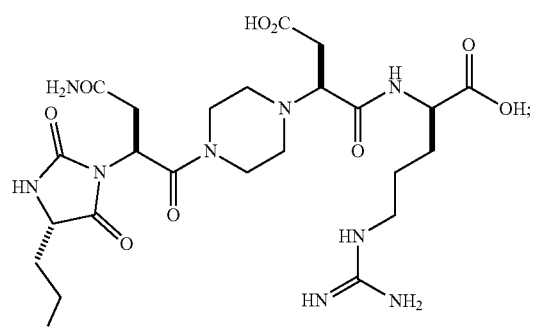
KB22879
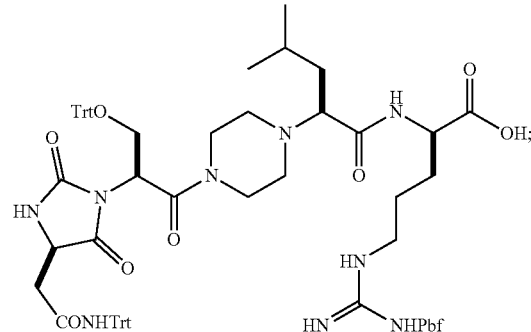
KB2280
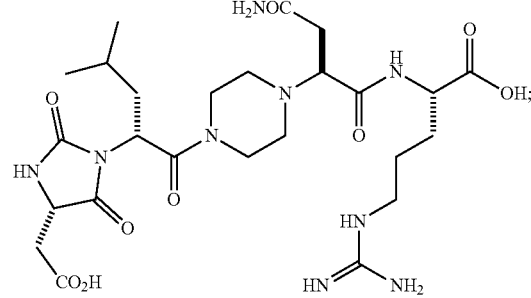

-continued
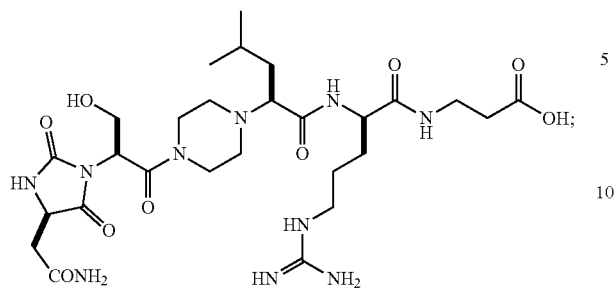
KB2281
and stereoisomers and pharmaceutically acceptable salts thereof.
15. A pharmaceutical composition, comprising a compound of claim 1, or a stereoisomer or pharmaceutically acceptable salt thereof, and a pharmaceutically acceptable carrier.
* * * * *